US007618813B2

(12) United States Patent
Lee et al.

(10) Patent No.: US 7,618,813 B2
(45) Date of Patent: Nov. 17, 2009

(54) MULTI-LAYERED PHOTOBIOREACTOR AND METHOD OF CULTURING PHOTOSYNTHETIC MICROORGANISMS USING THE SAME

(75) Inventors: Choul-Gyun Lee, Seoul (KR); In Soo Suh, Jesu-si (KR); Hyun-Na Joo, Gangwon-do (KR)

(73) Assignee: Inha-Industry Partnership Institute, Incheon (KR)

( * ) Notice: Subject to any disclaimer, the term of this patent is extended or adjusted under 35 U.S.C. 154(b) by 940 days.

(21) Appl. No.: 10/535,386

(22) PCT Filed: Feb. 16, 2004

(86) PCT No.: PCT/KR2004/000309

§ 371 (c)(1),
(2), (4) Date: May 17, 2005

(87) PCT Pub. No.: WO2005/059087

PCT Pub. Date: Jun. 30, 2005

(65) Prior Publication Data

US 2006/0035370 A1 Feb. 16, 2006

(30) Foreign Application Priority Data

Dec. 16, 2003 (KR) ...................... 10-2003-0092086

(51) Int. Cl.
*C12M 1/00* (2006.01)
*C12M 3/00* (2006.01)

(52) U.S. Cl. .............. 435/292.1; 435/257.1; 435/295.2; 47/1.4

(58) Field of Classification Search .............. 435/257.1, 435/257.2, 257.3, 257.4, 257.5, 257.6, 292.1, 435/294.1, 295.2, 296.1; 47/1.4
See application file for complete search history.

(56) References Cited

U.S. PATENT DOCUMENTS

| | | | | |
|---|---|---|---|---|
| 5,882,849 | A | | 3/1999 | Leonard et al. |
| 5,897,997 | A | * | 4/1999 | Louvel .................... 435/294.1 |
| 6,022,701 | A | | 2/2000 | Boussiba et al. |
| 6,571,735 | B1 | * | 6/2003 | Wilkinson .................. 119/215 |

FOREIGN PATENT DOCUMENTS

| | | |
|---|---|---|
| JP | 2000-060532 | 2/2000 |
| JP | 2001-309778 | 6/2001 |
| WO | 9800559 | 1/1998 |

* cited by examiner

*Primary Examiner*—William H Beisner
*Assistant Examiner*—Michael Hobbs
(74) *Attorney, Agent, or Firm*—Lucas & Mercanti, LLP

(57) ABSTRACT

Disclosed is a multi-layered photobioreactor capable of producing a useful metabolite simultaneously with the vegetative growth of a photosynthetic microorganism, including a first culture region (2) containing the microorganism and a culture medium to execute vegetative growth of the microorganism, and a second culture region (1) closely layered on a side surface of the first culture region and containing a culture medium and the microorganism to produce the useful metabolite. The two culture regions are separated from each other with a transparent partition, and the light sufficiently strong for induction of the useful metabolite production is irradiated to the first culture region, while the intensity of the light is reduced to a level proper to the microbial growth during a transmission of the light through the first culture region to arrive the second culture region. Also, the present invention discloses a method of culturing a photosynthetic microorganism using the photobioreactor.

16 Claims, 16 Drawing Sheets

■ : Outer Jacket(second culture region)

□ : Inner Core(first culture region)

■ : Outer Jacket(second culture region)

□ : Inner Core(first culture region)

■ : Outer Jacket(second culture region)

□ : Inner Core(first culture region)

■ : Outer Jacket(second culture region)

□ : Inner Core(first culture region)

■ : Outer Jacket(second culture region)

□ : Inner Core(first culture region)

■ : Outer Jacket(second culture region)

□ : Inner Core(first culture region)

MULTI-LAYERED PHOTOBIOREACTOR AND METHOD OF CULTURING PHOTOSYNTHETIC MICROORGANISMS USING THE SAME

This patent application claims the benefit of priority from Korean Patent Application No. 10-2003-0092086 filed Dec. 16, 2003 through PCT Application Serial No. PCT/KR2004/000309 filed Feb. 16, 2004, the contents of each of which are incorporated herein by reference.

TECHNICAL FIELD

The present invention relates to a multi-layered photobioreactor and a method of culturing a photosynthetic microorganism using the same. More particularly, the present invention relates to a multi-layered photobioreactor for culturing of a photosynthetic microorganism with two distinct environments which are optimal for the vegetative growth of the microorganism and the production of a useful metabolite by the microorganism, respectively, and a method of culturing a photosynthetic microorganism using such a photobioreactor.

PRIOR ART

Recently, algal biotechnology has received increasing interest in the world, and is becoming a frontier of the biotechnologies. Algal biotechnology is a field that finds and isolates various high-value useful metabolites from several photosynthetic microorganisms. The obtained useful metabolites are utilized as medicinal substances and health foods, such as highly valuable antibiotics, vitamins and physiologically active materials, dyes, such as carotenoids and biloprotein, purified chemicals, such as bioflocculant, polyols and carbohydrates, and alternative fuels, such as oils and carbohydrates.

Among the photosynthetic microorganisms, some require different environments for the vegetative growth and production of useful metabolites. Therefore, a two-phase process is typically applied for obtaining useful metabolites from the photosynthetic microorganisms having a life cycle of multiple stages. The two-staged process comprises maintaining an optimal growth condition for vegetative growth of a photosynthetic microorganism and maintaining a stressed condition suitable for production of a useful metabolite by the cultured microorganism at a stationary phase. The useful metabolites obtained as described above are called secondary metabolites or non-growth-associated products because of being produced during the stationary phase at which cell division stops.

Photosynthetic microorganisms having such a complex life cycle include *Haematococcus* sp., *Dunaliella* sp., *Chlorococcum* sp., *Chlorella* sp., *Acetabularia* sp., *Microcystis* sp., *Nostoc* sp., and *Oscillatoria* sp. In particular, the *Haematococcus* species produce astaxantin, which is used as an anti-oxidant and other biologically active functions.

For example, as described in U.S. Pat. Nos. 5,882,849 and 6,022,701, the production of high-value useful metabolites using photosynthetic microorganisms is achieved by a two-stage cultivation process, which employs two cultivation baths with different environmental conditions for vegetative growth and production of useful metabolites. In detail, at the first stage, a large-scale cultivation of the microorganisms is rapidly achieved by maintaining optimal growth conditions suitable for vegetative growth in a cultivation bath. At the second stage, the useful metabolites are effectively produced using the biomass obtained in the first stage by maintaining optimal environmental conditions for production of the useful metabolites (secondary metabolites) in another cultivation bath.

The conventional cultivation techniques, which employ the two separate cultivation baths with different environments suitable for the vegetative cell growth and the production of useful metabolites, respectively, have an economical benefit in terms of facilitating relatively high-density cultivations of photosynthetic microorganisms and of preventing contamination with unwanted microorganisms, compared to the outdoor cultures in a pond system or in a raceway circulating culture medium using a paddle wheel.

However, the conventional cultivation techniques have significant problems to be solved, which will be described as follows. Since the two cultivation baths for the vegetative growth in the first stage and the production of useful metabolites in the second stage are separately prepared, the conventional techniques require high land cost or installation cost and high operation cost, as well as highly skilled engineers capable of complex operations. For this reason, the conventional techniques cannot be applied optimally and efficiently for the industrialized production of high-value useful metabolites from photosynthetic microorganisms.

DISCLOSURE OF THE INVENTION

Conducted by the present invention, the through and intensive research aiming to solve the problems encountered in the prior art resulted in the finding that, upon production of a high-value useful metabolite using a specific photosynthetic microorganism, a photobioreactor with the inside thereof divided into a vegetative growth region and a useful-metabolite production region has the effects of reducing labor and energy required for the vegetative growth and the production of the useful metabolite and economically yielding the useful metabolite.

It is therefore an object of the present invention to provide a multi-layered photobioreactor that is labor-saving in the cultivation of a photosynthetic microorganism and economical in the production of a useful metabolite by applying the same light source for both stages at the same time.

It is another object of the present invention to provide a method of culturing a photosynthetic microorganism using the multi-layered photobioreactor.

To achieve the above objects, the present invention provides a multi-layered photobioreactor, including at least one first culture region containing both a microorganism and a culture medium therein to execute vegetative growth of the microorganism; at least one second culture region closely layered on a side surface of the first culture region and containing both a culture medium and a microorganism therein to produce a useful metabolite; and a transparent partition placed between the first and second culture regions to separate the first and second culture regions from each other, wherein the first and second culture regions are provided in an inside portion and an outside portion of the photobioreactor, respectively, to allow sun light or artificial light irradiated to the photobioreactor for cultivation to sequentially pass through the second culture region and the transparent partition to reach the first culture region.

In addition, the present invention provides a multi-layered photobioreactor including a first culture region for vegetative cell growth, a second culture region for production of a useful metabolite, a transparent partition, and a light irradiation unit to irradiate light to the photobioreactor, wherein the first culture region is provided to be not in contact with the light irradiation unit, while the second culture region is provided to be in contact with the light irradiation unit, thus allowing the light emitted from the light irradiation unit to sequentially pass through the second culture region and the transparent partition to reach the first culture region.

Further, the present invention provides a method of culturing photosynthetic microorganisms using the multi-layered photobioreactor.

BRIEF DESCRIPTION OF THE DRAWINGS

The above and other objects, features and other advantages of the present invention will be more clearly understood from the following detailed description taken in conjunction with the accompanying drawings, in which.

BEST MODES FOR CARRYING OUT THE INVENTION

Figure 1A:
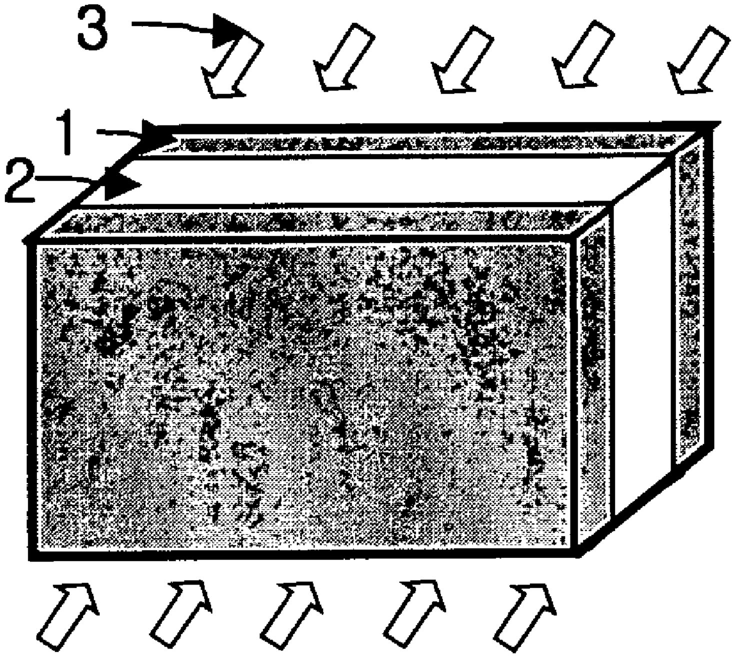
FIGS. 1*a* and 1*b* are a perspective view and a cross-sectional view of a double-layered flat-plate-type photobioreactor with an external irradiation, according to an embodiment of the present invention.

The present invention provides a multi-layered photobioreactor.

The multi-layered photobioreactor of the present invention includes a first culture region containing a microorganism and a culture medium to execute vegetative growth of the microorganism, and a second culture region closely layered on a side surface of the first culture region and containing a culture medium and a microorganism to produce a useful metabolite, wherein the two culture regions are separated from each other with a transparent partition.

Due to the aforementioned structure of the multi-layered photobioreactor of the present invention, excessive light energy is supplied to the second culture region to produce a useful metabolite, which is positioned to be directly exposed to light, and thus induce a specific microorganism in the second culture region to utilize the high-intensity light energy and to accumulate metabolites. During a transmission through the second culture region, the light energy is weakened by mutual shading effects of biomass in the culture medium and released with a low intensity to an opposite surface to the light-irradiated surface of the second culture region. The low-intensity residual light energy is then supplied to a photosynthetic microorganism present in the first culture region layered on a side surface of the second culture region and positioned in an inner part of the multi-layered photobioreactor, wherein the microorganism carries out photosynthesis using the supplied light for vegetative growth.

The light energy decreases logarithmically with a distance from a light source (as δ increases) and with the concentration of a microorganism in the culture medium (as ρ increases) according to the Beer-Lambert's Law, as described in the following Equation 1:

$$I=I_o \exp(-\sigma\rho\delta) \quad \text{[Equation 1]}$$

wherein, I is the light intensity of light transmitted through a light-absorbing system, $I_o$ is the initial intensity from a light source, σ is the absorption coefficient, ρ is the concentration of a microorganism in the light-absorbing system, and δ is the thickness of the light-absorbing system.

While the light is transmitted through the second culture region to produce a useful metabolite, the light attenuation is affected by the initial intensity ($I_o$), the concentration (ρ) of the biomass in the second culture region, the size of the microorganism and the content of pigments and the light-penetrating depth (δ). In addition, the light energy should be supplied to the first culture region to execute the vegetative cell growth at levels suitable for the vegetative cell growth. When the light energy is supplied in very low quantities, the useful metabolite is not accumulated in the second culture region. In contrast, when the amount of the supplied light energy is very high, the vegetative cell growth in the first culture region is inhibited, and light energy that is not used in photosynthesis is converted into heat energy, thus increasing the temperature of the culture medium.

The representative example of the light irradiated to the multi-layered photobioreactor of the present invention is sunlight. To allow sunlight to pass through the second culture region to produce a useful metabolite and pass through the transparent partition to arrive the first culture region to execute the vegetative cell growth, the second culture region is positioned at an outer region of the photobioreactor while the first culture region is positioned at an inner region of the photobioreactor.

In addition to sunlight, the present invention includes a light irradiation unit as an artificial light source. To allow the light emitted from the light irradiation unit to transmit through the second culture region to produce a useful metabolite and pass through the transparent partition to arrive the first culture region to execute the vegetative cell growth, the light irradiation unit is provided at a position of being adjacent to the second culture region while being not adjacent to the first culture region. The light source useful in the present invention may be one or more selected from among fluorescent lamps, halogen lamps, optical fibers, neon tubes, light-emitting diodes and other photosynthetically active radiations (PARs). That is, the photobioreactor may utilize sunlight alone or in combination with one or more artificial light sources. In the latter case, while sunlight is used as a base light energy source, according to seasonal (especially in winter), temporal (especially at night) and meteorological (especially upon cloudy weather) factors and the vegetative cell growth and the metabolite accumulation, deficient light energy is supplemented by using the additional light sources. In detail, as shown in FIGS. 6, 7 and 10, when the second culture region to produce a useful metabolite is formed at an outmost surface and an innermost surface of the photobioreactor, sunlight is irradiated to the second culture region at the outmost surface of the photobioreactor, while an artificial light from a light irradiation unit is irradiated to another second culture region provided at the innermost surface of the photobioreactor.

In addition, in order to prevent the overall light intensity from being badly affected, for example, by short circuit, the light irradiation unit comprises a plurality of independent units which are operated with separate power sources.

While utilizing the artificial light sources, the supplied amount, wavelength, and irradiation time and irradiation period of the light may be controlled to be suitable for the vegetative cell growth in the second culture region or the production of the useful metabolite in the first culture region of the multi-layered photobioreactor, but are not limited to the above mentioned control.

The photobioreactor of the present invention may be designed to have various shapes. Preferably, the photobioreactor may be designed to have a shape selected from the group consisting of a rectangular flat-plate shape, a cylindrical shape, a tubular shape and other three-dimensional geometries.

In addition, to achieve the scale-up in culture volumes for industrial application, the photobioreactor may be used as a unit module for continuous stacking. If desired, the photobioreactor of a flat-plate type and the light source may be arranged in an one-dimensional multi-arrangement of a sandwich form, while the photobioreactor of an upright cylinder type and the light source may be arranged in a two-dimensional multi-arrangement. In addition, the photobioreactor of the present invention may be arranged in the three-dimensional multi-arrangement. The volume of the photobioreactor is preferably determined by the size of the bioprocess for production of useful metabolites and the area of the plant site. Also, the scale-down in culture volumes may be easily achieved by removing some unit modules comprising a photobioreactor and a light source from the multi-arranged construction or by blocking a pipe-line connecting the unit modules.

On the other hand, to inject gas to lower parts of the first and second culture regions and thus allow supplied $CO_2$ and culture medium to flow upwardly, the photobioreactor may be produced in the form of an air-lift, or a stirred-tank additionally equipped with a mechanical agitation means (e.g., an impeller and a magnetic stirrer).

In summer, the temperature of the culture medium is increased by heat derived from the light source, high exterior temperature, metabolic heat of the cultured microorganims and heat energy to which light energy not absorbed by the microorganisms is converted. In contrast, in winter or at night, since the cultivation temperature is dropped below optimal ranges, the vegetative cell growth and production of useful metabolites are inhibited. In this regard, if the temperature of the culture medium is desired to maintain within ranges optimal for the growth of photosynthetic microorganisms and the production of useful metabolites, heat exchangers and sprayers to control the temperature by use of cold water or hot water or sun screen units may be used.

With reference to the accompanying drawings, the preferred embodiments of the photobioreactor of the present invention will be described.

In a first embodiment, the present invention provides a photobioreactor utilizing sunlight.

Figure 1B:
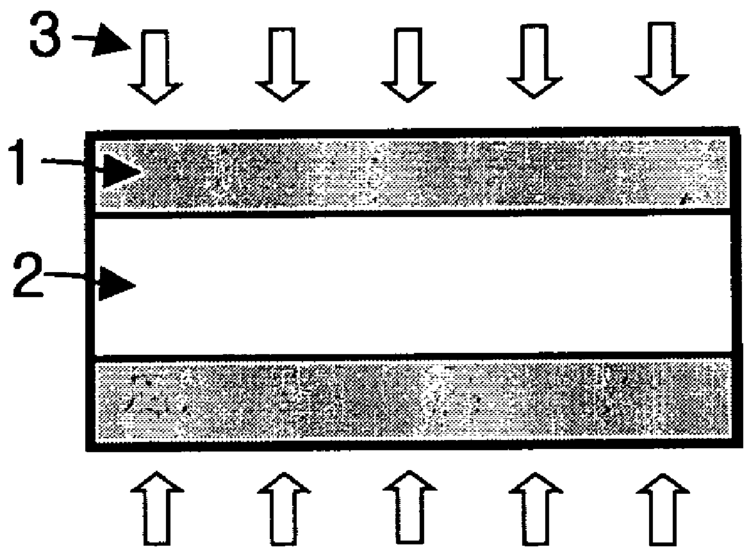

FIGS. 1*a* and 1*b* illustrate a double-layered flat-plate-type photobioreactor with an external irradiation. The light 3 is irradiated to the opposite surfaces of the flat-plate-type photobioreactor. Two second culture regions 1 to produce useful metabolites are formed at the opposite side portions of the photobioreactor, which include the two light-irradiated surfaces. A first culture region 2 to execute the vegetative cell growth is closely layered between the two first culture regions 1. The light is transmitted through the second culture regions 1 to the first culture region 2.

Figure 2A:
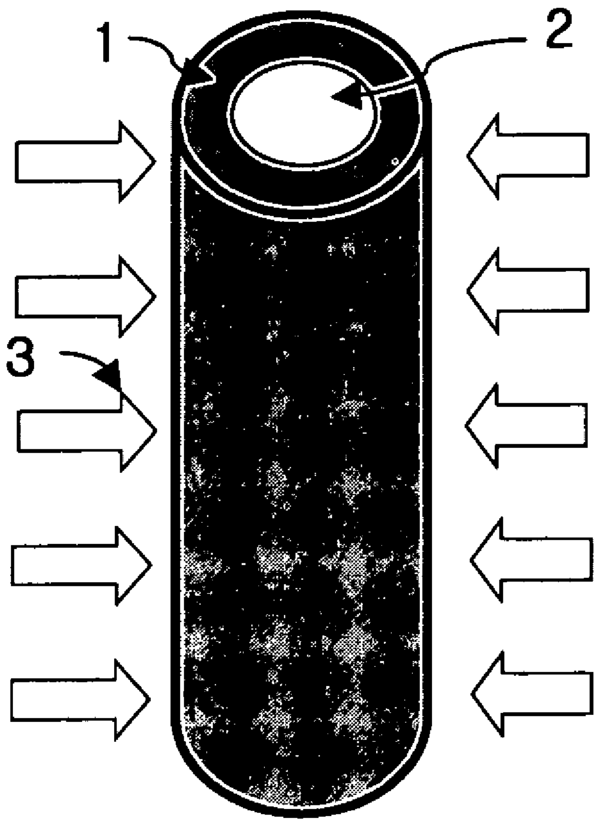
FIGS. 2*a* and 2*b* are a perspective view and a cross-sectional view of a double-layered upright-cylindrical photobioreactor with an external irradiation, according to another embodiment of the present invention.
Figure 2B:
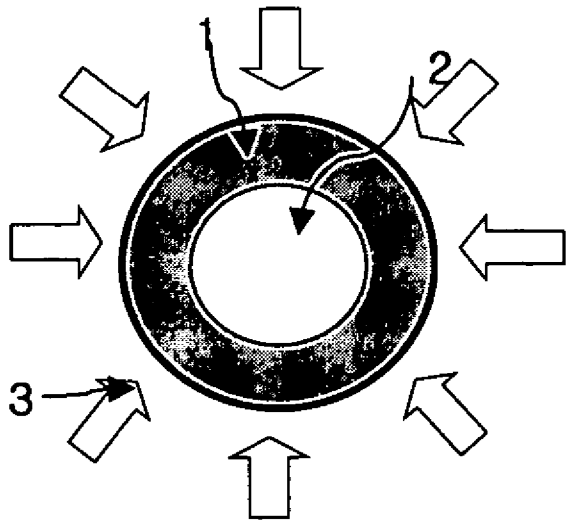

FIGS. 2*a* and 2*b* illustrate a double-layered upright-cylindrical photobioreactor with an external irradiation. The light 3 is irradiated to the external surface of the upright cylindrical photobioreactor. A second culture region 1 to produce a useful metabolite is formed around the outside portion of the photobioreactor, which includes the light-irradiated surface, thus forming a ring-shaped cross-sectrion, while a first culture region 2 to execute the vegetative cell growth is closely placed inside of the first culture region 1. The light is transmitted through the second culture region 1 to the first culture region 2.

Figure 3A:
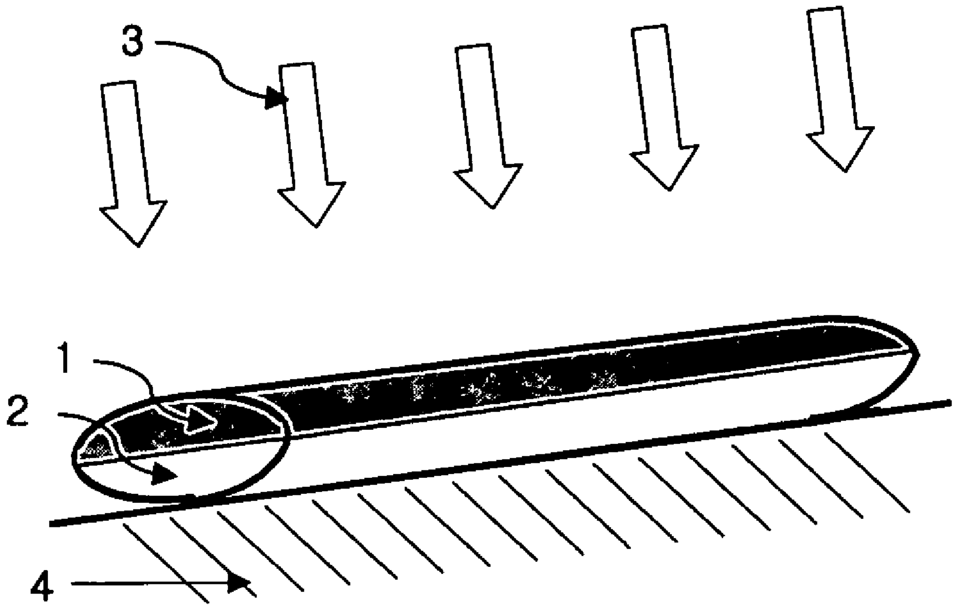
FIGS. 3*a* and 3*b* are a perspective view and a cross-sectional view of a tubular photobioreactor, which utilizes sunlight, according to a further embodiment of the present invention.
Figure 3B:
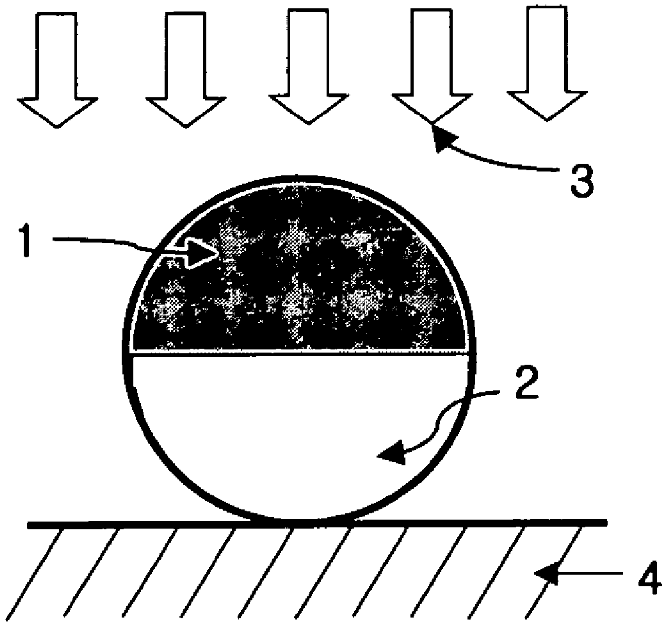

FIGS. 3*a* and 3*b* illustrate a tubular photobioreactor, which utilizes sunlight upon exterior cultivation. The sunlight 3 is directly irradiated to an outer surface of a second culture region 1 which produces a useful metabolite and is placed at a portion of the photobioreactor to which the sunlight 3 is irradiated. A first culture region 2 to execute the vegetative cell growth is closely layered on a lower side surface of the first culture region 1. The sunlight is transmitted through the second culture region 1 to the first culture region 2 contacted with ground 4.

Figure 4A:
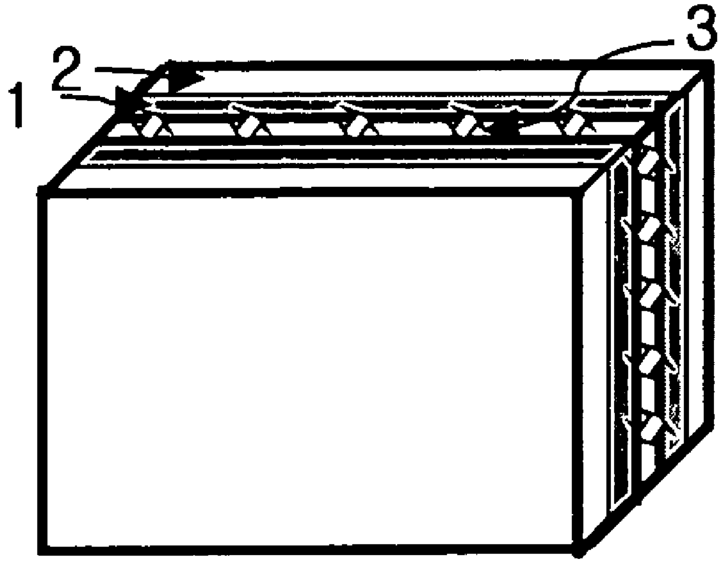
FIGS. 4*a* and 4*b* are a perspective view and a cross-sectional view of a double-layered flat-plate-type photobioreactor with an internal irradiation, according to still another embodiment of the present invention.
Figure 4B:
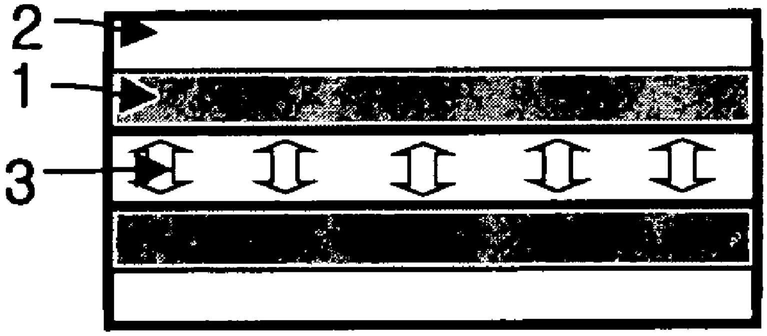

FIGS. 4*a* and 4*b* illustrate a double-layered flat-plate-type photobioreactor with an internal irradiation. A light irradiation unit to supply light 3 in the photobioreactor is positioned in a central part of a flat-plate-type photobioreactor. Two second culture regions 1 to produce useful metabolites are formed in the photobioreactor at opposite sides of the light irradiation unit, which include the light-irradiated surfaces. Two first culture regions 2 to execute the vegetative cell growth are closely layered on the outside surfaces of the first culture regions 1, respectively. The light is transmitted through the second culture regions 1 to the first culture regions 2.

Figure 5A:
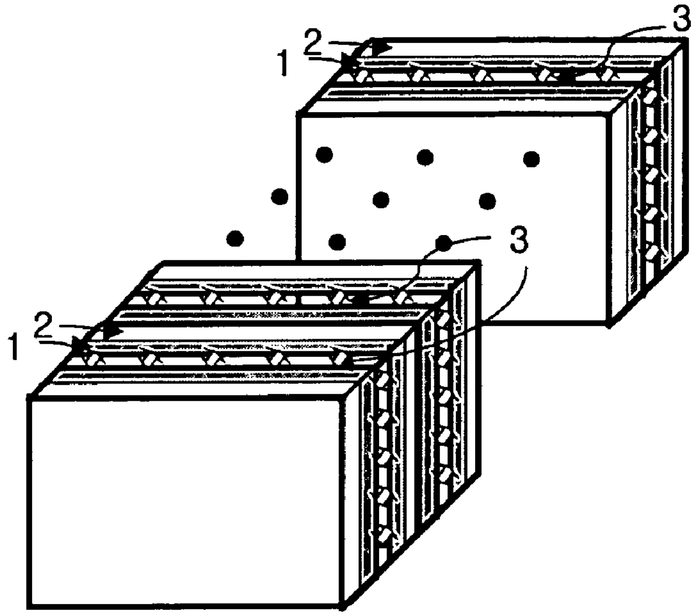
FIGS. 5*a* and 5*b* are a perspective view and a cross-sectional view of a consecutive arrangement of the double-layered flat-plate-type photobioreactors with the internal irradiation of FIGS. 4*a* and 4*b;*
Figure 5B:
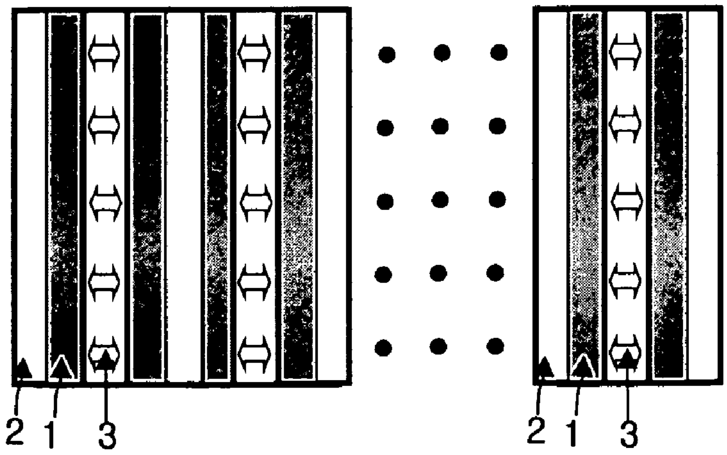

FIGS. 5*a* and 5*b* illustrate a consecutive arrangement of the double-layered flat-plate-type multi-layered photobioreactors with the internal irradiation of FIGS. 4*a* and 4*b*, wherein each photobioreactor is used as a unit module. The arrangement of the unit modules and the light irradiation direction are illustratively shown in FIGS. 5*a* and 5*b*.

Figure 6A:
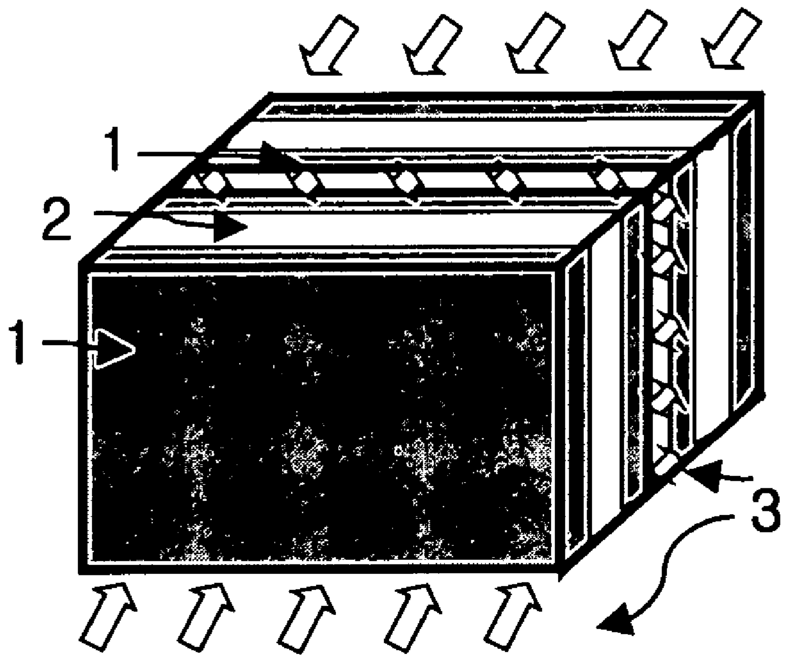
FIGS. 6*a* and 6*b* are a perspective view and a cross-sectional view of a triple-layered flat-plate-type photobioreactor with both internal and external irradiations, according to still another embodiment of the present invention.
Figure 6B:
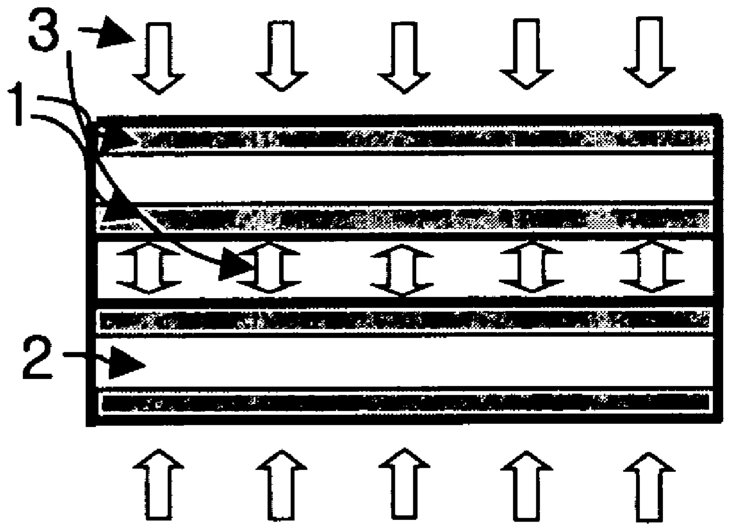

FIGS. 6*a* and 6*b* illustrate a triple-layered flat-plate-type multi-layered photobioreactor with both internal and external irradiations, which is a composite form of the photobioreactors of FIGS. 1 and 4. The light 3 is irradiated to both the opposite side surfaces and the central part of the flat-plate-type multi-layered photobioreactor. Second culture regions 1 to produce useful metabolites are formed at regions including the light-irradiated surfaces of the photobioreactor, while first culture regions 2 to execute the vegetative cell growth are closely layered between the second culture regions 1. The light is transmitted through the second culture regions 1 to the first culture regions 2.

Figure 7A:
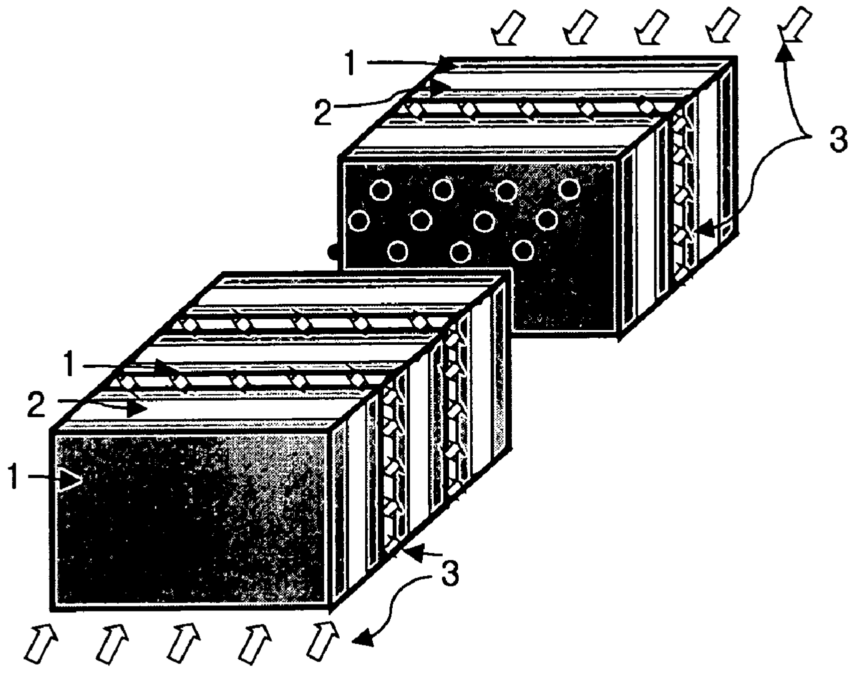
FIGS. 7*a* and 7*b* are a perspective view and a cross-sectional view of a consecutive arrangement of the triple-layered flat-plate-type photobioreactors with the internal and external irradiations of FIGS. 6*a* and 6*b;*
Figure 7B:
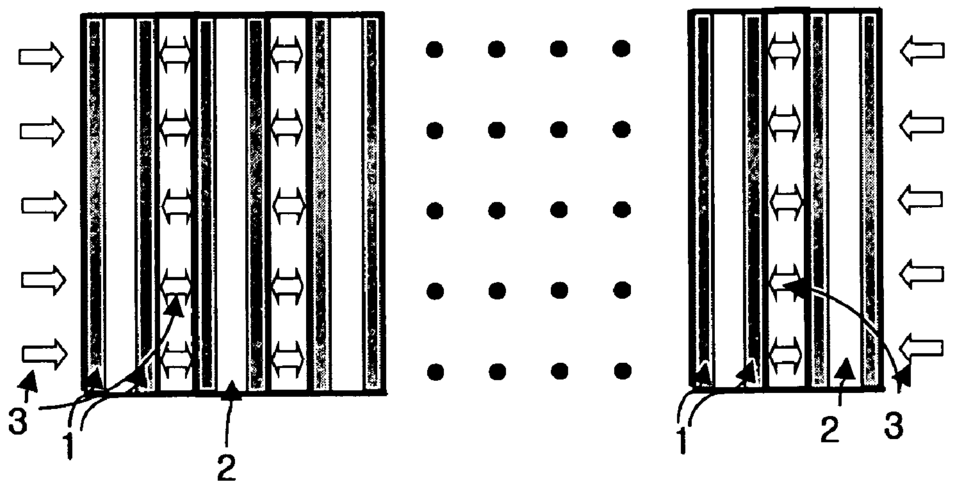

FIGS. 7*a* and 7*b* illustrate a consecutive arrangement of the triple-layered flat-plate-type multi-layered photobioreactors with the internal and external irradiations of FIGS. 6*a* and 6*b*, wherein each photobioreactor is used as a unit module. The arrangement of the unit modules and the light irradiation direction are illustratively shown in FIGS. 7*a* and 7*b*.

Figure 8A:
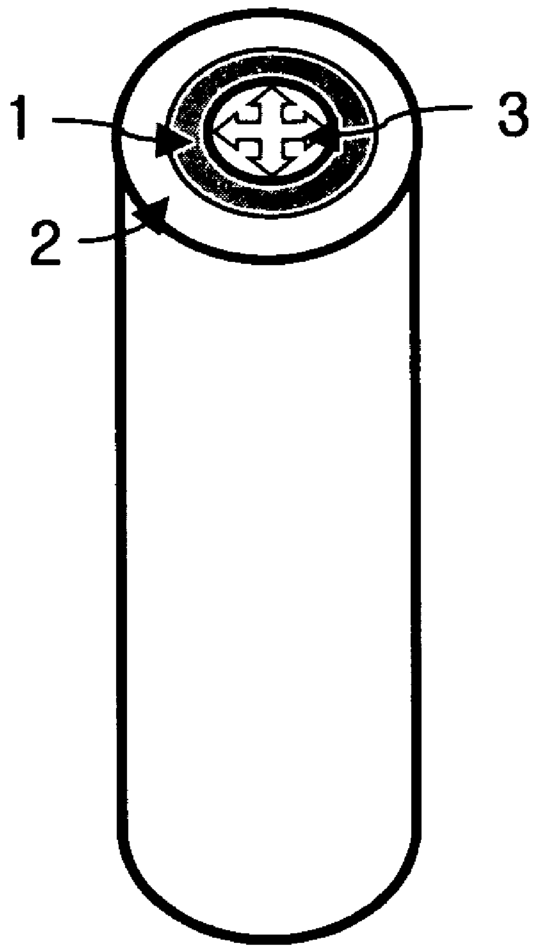
FIGS. 8*a* and 8*b* are a perspective view and a cross-sectional view of a double-layered upright-cylindrical photobioreactor with an internal irradiation, according to still another embodiment of the present invention.
Figure 8B:
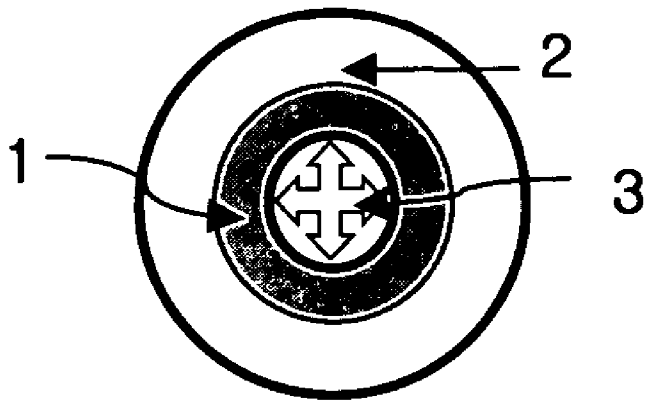

FIGS. 8*a* and 8*b* illustrate a double-layered upright-cylindrical multi-layered photobioreactor with an internal irradiation. A light irradiation unit to supply the light 3 in the photobioreactor is positioned in a central part of the upright-cylindrical multi-layered photobioreactor. A second culture region 1 to produce a useful metabolite is formed in the inner region which is around the light irradiation unit and includes the light-irradiated surface of the photobioreactor. A first culture region 2 to execute the vegetative cell growth is closely layered on the outside surface of the first culture region 1. The light is transmitted through the second culture region 1 to the first culture region 2.

Figure 9A:
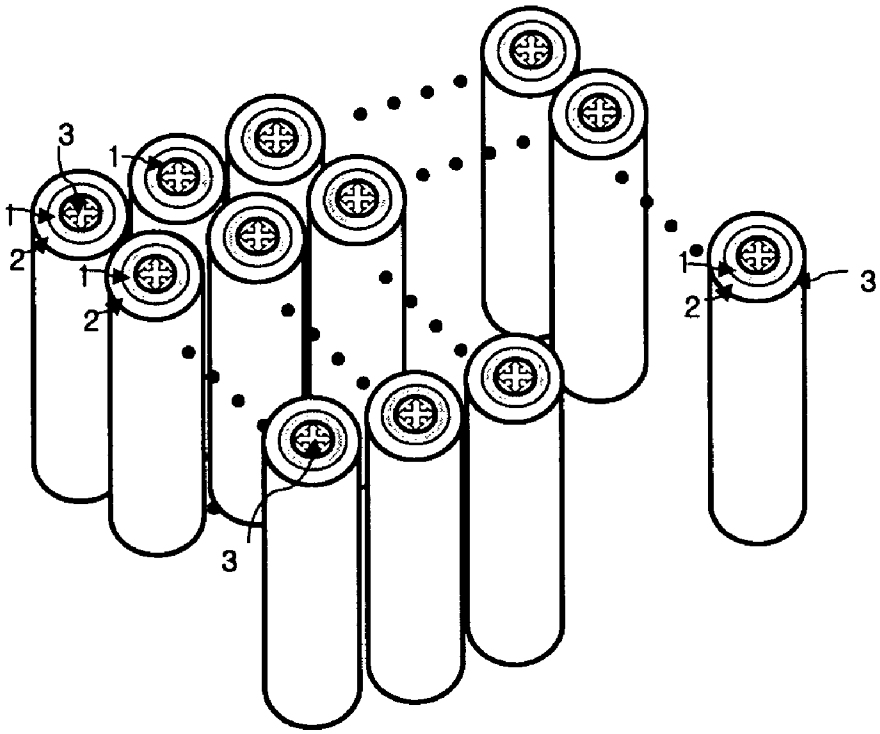
FIGS. 9*a* and 9*b* are a perspective view and a cross-sectional view of a consecutive arrangement of the double-layered upright-cylindrical photobioreactors with the internal irradiation of FIGS. 8*a* and 8*b;*
Figure 9B:
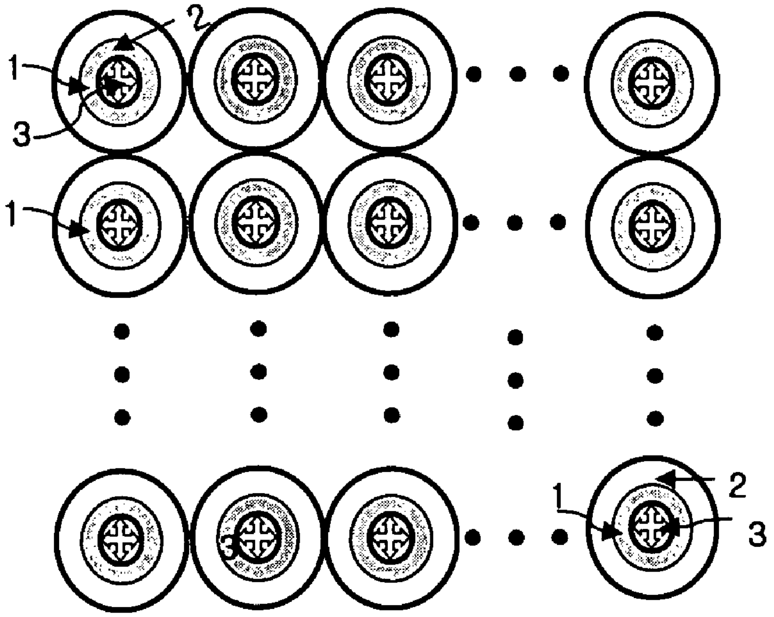

FIGS. 9*a* and 9*b* illustrate a consecutive arrangement of the double-layered upright-cylindrical photobioreactors with the internal irradiation, wherein each photobioreactor is used as a unit module. The arrangement of the unit modules and the light irradiation direction are illustratively shown in FIGS. 9*a* and 9*b*.

Figure 10A:
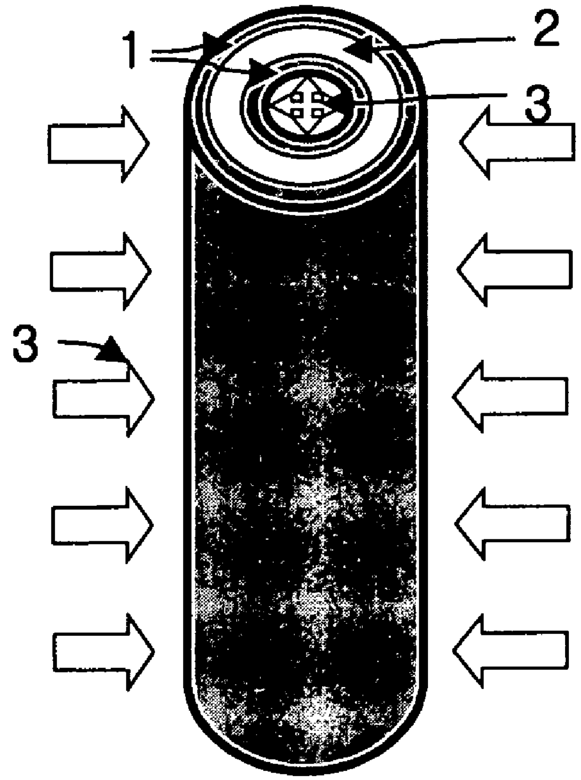
FIGS. 10*a* and 10*b* are a perspective view and a cross-sectional view of a triple-layered cylindrical photobioreactor with both internal and external irradiations, according to still another embodiment of the present invention.
Figure 10B:
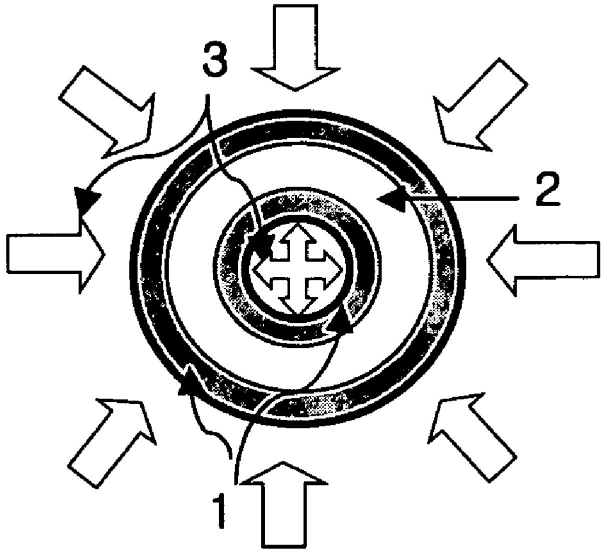

FIGS. 10*a* and 10*b* illustrate a triple-layered upright-cylindrical multi-layered photobioreactor with both internal and external irradiations. Two light irradiation units to supply the light 3 in the photobioreactor are in the exterior and the central part of the upright-cylindrical multi-layered photobioreactor. One second culture region 1 to produce a useful metabolite is formed in the outside portion which includes the light-irradiated surface of the photobioreactor. Another second culture region 1 is formed in the inner region which is around the light irradiation-unit at the central part of the photobioreactor and includes the light-irradiated surface of the photobioreactor therein. A first culture region 2 to execute the vegetative cell growth is closely layered between the second culture regions 1. The light is transmitted through the second culture regions 1 to the first culture region 2.

Figure 11A:
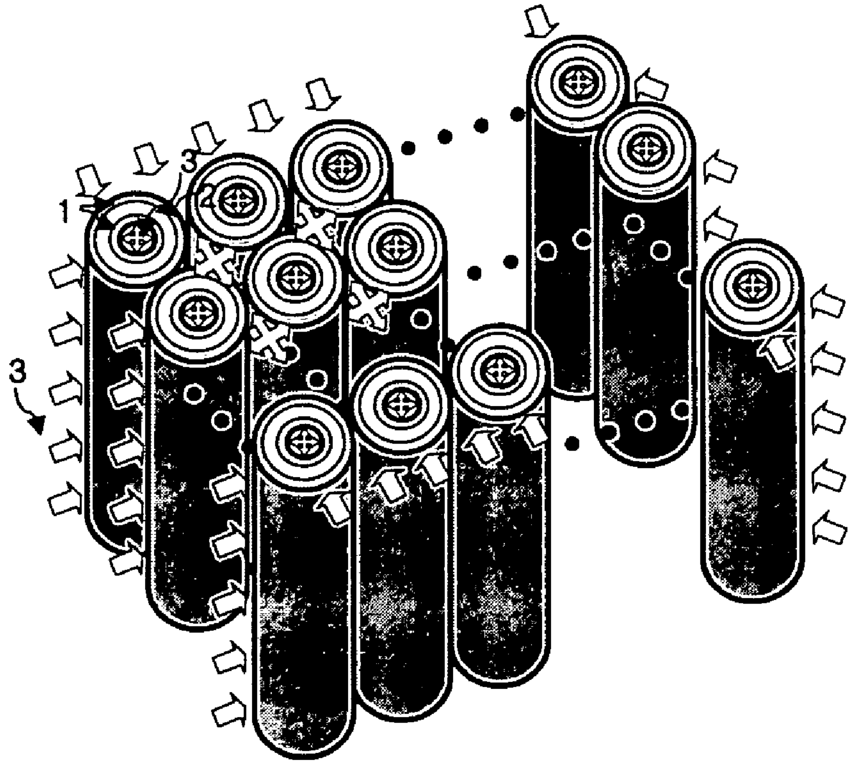
FIGS. 11*a* and 11*b* are a perspective view and a cross-sectional view of a consecutive arrangement of the triple-layered upright-cylindrical photobioreactors with the internal and external irradiations of FIGS. 10*a* and 10*b;*
Figure 11B:
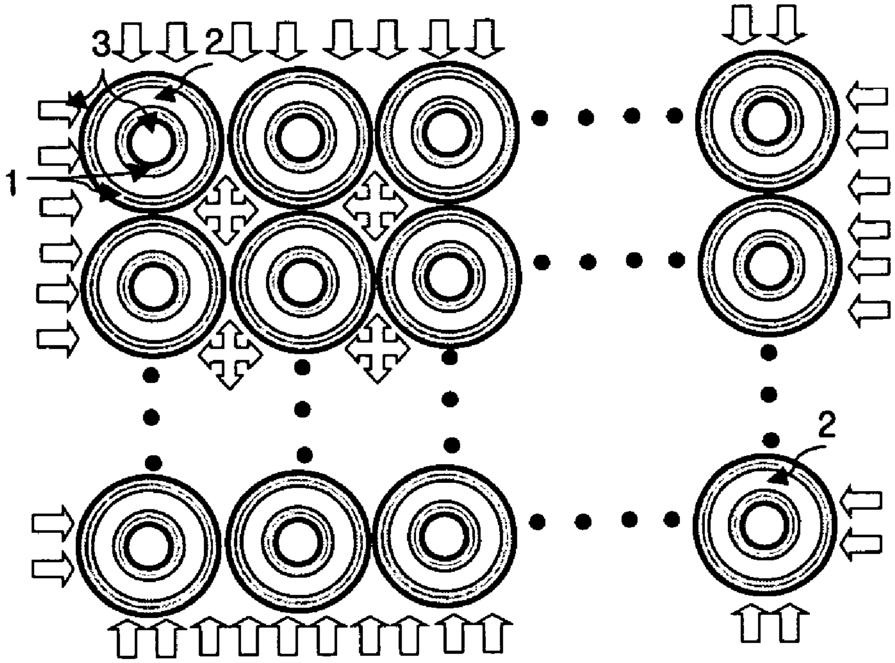

FIGS. 11*a* and 11*b* illustrate a consecutive arrangement of the triple-layered upright-cylindrical photobioreactors, wherein each photobioreactor is used as a unit module. The arrangement of the unit modules and the light irradiation direction are illustratively shown in FIGS. 11*a* and 11*b*.

In addition, the present invention provides a method of culturing a photosynthetic microorganism using the multi-layered photobioreactor. In detail, the present method is based on batch, continuous and fed-batch cultures. However, such culture techniques are provided only to illustrate the present invention, and the present invention is not limited to these culture techniques.

In more detail, in a batch culture using the multi-layered photobioreactor of the present invention, the present invention provides a method of culturing a photosynthetic microorganism, including injecting a photosynthetic microorganism into the first culture region to execute the vegetative cell growth and the second culture region to produce a useful metabolite (step 1); irradiating the light to the second culture region to proliferate the photosynthetic microorganism and to maximize the accumulation of the useful metabolite (step 2); and harvesting the cultured photosynthetic microorganism from the first and second culture regions (step 3).

In step 1 of the batch culture, a photosynthetic microorganism is injected into each culture region in the photobioreactor of the present invention. Herein, the microorganism is inoculated to the first and second culture regions at equal or different concentrations according to the intended use. Also, the microorganism can be used after being adjusted to the light intensity of each culture region. The microorganism inoculated to both culture regions is primarily allowed for the vegetative growth. The inoculation should be performed at densities not causing the mutual shading effects, which bring about a severe decrease in the light intensity. Thus, the inoculum concentration may vary depending on the cell size. For example, a *Chlorella* species is inoculated at densities of $10^3$ to $10^8$ cells/ml, while a *Haematococcus* species is inoculated at densities of $10^3$ to $10^7$ cells/ml. The culture medium may be determined according to the photosynthetic microorganism.

In step 2 of the batch culture, in order to induce the vegetative cell growth and the production of the useful metabolite, light is irradiated to the second culture region to produce a useful metabolite. Herein, the initial light is supplied at intensities optimal for the vegetative growth of the photosynthetic microorganism to allow for the vegetative growth of the inoculated photosynthetic microorganism. For example, in the case of *Haematococcus*, the light is supplied at intensities of 40 to 200 $\mu mol/m^2/s$ at the light-irradiated surface of the second culture region to produce a useful metabolite. The light is attenuated to 10 to 50 $\mu mol/m^2/s$ when transmitted through the second culture region to the first culture region to execute the vegetative cell growth. In addition, pH, temperature and injection amounts of gas may be determined according to photosynthetic microorganisms. For example, a *Haematococcus* species is grown at 25° C. under pH 7.0 and 5% $CO_2$, which is injected at a rate of 10 ml/min along with 95% air.

When the light of the above intensity is irradiated to the photobioreactor for a predetermined period, the photosynthetic microorganism in the second culture region reaches a stationary phase at which the vegetative cell growth stops. At the stationary phase, the microorganism accumulates secondary metabolites. The stationary phase varies according to the initial light intensity, the kinds of inoculated photosynthetic microorganisms and the inoculum concentration. Under the conditions of one example to be described later, the stationary phase was found to be maintained for 10 days, while astaxanthin accumulation was increased to 20-360 mg/L (see, FIGS. 13*c* and 13*d*).

After the stationary phase, to form an environment (stressed environment) optimal for the production of the useful metabolite, the light of relatively high intensity is irradiated to the photobioreactor, in comparison with the case that light is irradiated for the vegetative cell growth. The light intensity optimal for the production of the useful metabolite may vary depending on the photosynthetic microorganisms. For example, in the case of *Haematococcus*, the light intensity optimal for the astaxanthin production ranges from 200 to 2,000 $\mu mol/m^2/s$. After the application of the high-intensity light, the photosynthetic microorganism in the first and second culture regions displays different growth properties. In detail, the photosynthetic microorganism in the second culture region, irradiated with the high-intensity light, accumulates the useful metabolite in high concentrations, while the microorganism in the first culture region is irradiated with the light attenuated to the intensity suitable for the vegetative cell growth. For example, in the case of *Haematococcus* cells, the surface light intensity is reduced to 10-100 $\mu mol/m^2/s$, at which the cells undergo the vegetative growth. These results are given in FIGS. 14*a* and 14*b*. As described above, the light is irradiated to the photobioreactor at high intensities suitable for primarily inducing a photosynthetic microorganism to produce and accumulate a useful metabolite. After being transmitted through the region to produce a useful metabolite, the light is utilized for the vegetative cell growth. This method maximizes the efficiency of the light supplied to the photobioreactor.

In step 3 of the batch culture, the biomass is harvested from the first culture region to produce a useful metabolite when the useful metabolite is accumulated at maximum levels. Then, the useful metabolite is isolated from the biomass, purified and concentrated. The biomass in the first culture region to execute the vegetative cell growth is used as an inoculum in the next batch culture.

In the batch culture of a photosynthetic microorganism using the multi-layered photobioreactor, nutrients are supplied temporarily or consecutively.

In a continuous culture using the multi-layered photobioreactor of the present invention, the present invention provides a method of culturing a photosynthetic microorganism, including transferring the photosynthetic microorganism grown in the first culture region to execute the vegetative cell growth by the batch culture to the second culture region to produce a useful metabolite and injecting newly subcultured cells of the photosynthetic microorganism to the first culture region (step 1); irradiating the light to the second culture region to proliferate the photosynthetic microorganism and accumulate the useful metabolite (step 2); and harvesting the photosynthetic microorganism from the second culture region and repeating steps 2 and 3 (step 3).

In step 1 of the continuous culture, like in step 1 of the batch culture, a photosynthetic microorganism is introduced into each culture region of the photobioreactor. In detail, after the batch culture, in which the photosynthetic microorganism, which had accumulated the useful metabolite, has been harvested from the second culture region, the photosynthetic microorganism in the first culture region is transferred to the second culture region. For the vegetative growth, the photosynthetic microorganism is newly subcultured, harvested and injected into the first culture region along with culture medium. Alternatively, a part of the photosynthetic microorganism grown in the first culture region is transferred to the second culture region, while the microorganism remaining in the first culture region is refed with fresh culture medium to run a new cultivation.

Herein, the photosynthetic microorganism is transported by a peristaltic pump or air pressure. The peristaltic pump pushes the culture fluid including the high-density biomass in the first culture region into the second culture region through a shrinkable tube. In the case of using the air pressure, the culture fluid including the cells is collected from the first culture region, and then transferred to the second culture region by pushing up by the air pressure. Using the aforementioned methods, the newly subcultured cells are injected to the first culture region. These methods allow for continuous culture of the photosynthetic microorganism.

In step 2 of the continuous culture, the light is irradiated to the second culture region to produce a useful metabolite. Like step 2 of the batch culture, the light is supplied at high intensities to form an environment (stressed environment) optimal for the production of the useful metabolite, and preferably, at the same intensity as in the late stage of step 2 of the batch culture. In this case, identical effectiveness may be obtained.

Step 3 of the continuous culture is an intermediate step for consecutive or mass production of the photosynthetic microorganism, at which steps 1 and 2 of the continuous culture are repeated. In detail, in step 3 of the continuous culture, step 1 of the continuous culture, at which the photosynthetic microorganism grown in the first culture region is transferred to the second culture region, followed by the injection of newly subcultured cells of the microorganism to the first culture region, and step 2 of the continuous culture, at which the high-intensity light is irradiated to the photobioreactor to perform the accumulation of a useful metabolite simultaneously with the vegetative cell growth, are repeated. Therefore, step 3 of the continuous culture allows for consecutive and mass production of a photosynthetic microorganism accumulating a useful metabolite.

In a fed-batch culture using the multi-layered photobioreactor of the present invention, when nutrients are exhausted with the progress of the batch and continuous cultures, nutrients need to be additionally supplied to the photobioreactor in order to maintain concentrations suitable for the vegetative growth of a photosynthetic microorganism and the production of a useful metabolite by the microorganism. For example, maintenance of nitrogen concentration at the initial level is effective in the vegetative growth of *Haematococcus* (Enzyme Microbial Technol., 2003, 33: 403-409). Therefore, the fed-batch culture of *Haematococcus* species is preferably performed with addition of a nitrogen source to the first culture region to execute the vegetative cell growth.

The photosynthetic microorganism applicable to the multi-layered photobioreactor and the culturing method using the photobioreactor according to the present invention includes all photosynthetic microorganisms exhibiting a difference in environments optimal for the vegetative cell growth and the production of useful metabolites, which are exemplified by *Haematococcus* sp., *Dunaliella* sp., *Chlorococcum* sp., *Chlorella* sp., *Acetabularia* sp., *Microcystis* sp., *Nostoc* sp., and *Oscillatoria* sp.

The present invention will be explained in more detail with reference to the following examples in conjunction with the accompanying drawings. However, the following examples are provided only to illustrate the present invention, and the present invention is not limited to the examples.

EXAMPLE 1

Culturing of a Photosynthetic Microorganism

Figure 12A:
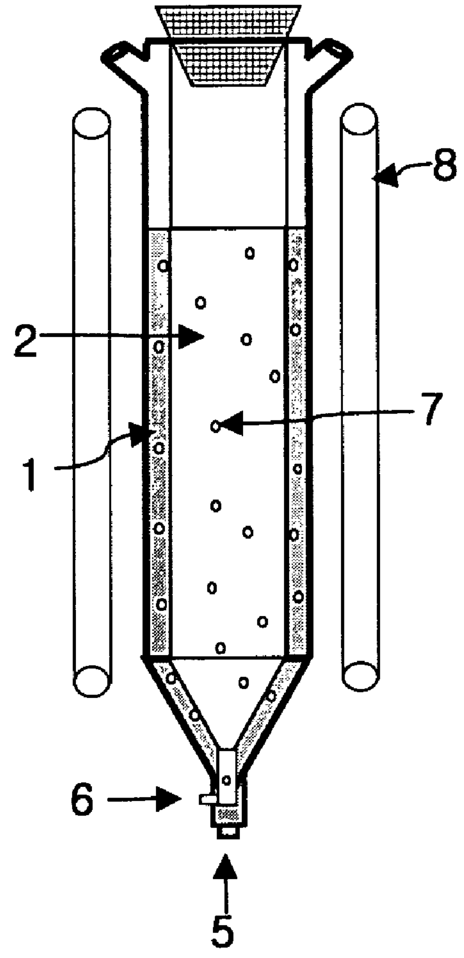
FIGS. 12*a* and 12*b* are a perspective view and a cross-sectional view of a double-layered upright-cylindrical air-lift photobioreactor equipped with external illuminants, where the gas is injected to the photobioreactor through its lower part.
Figure 12B:
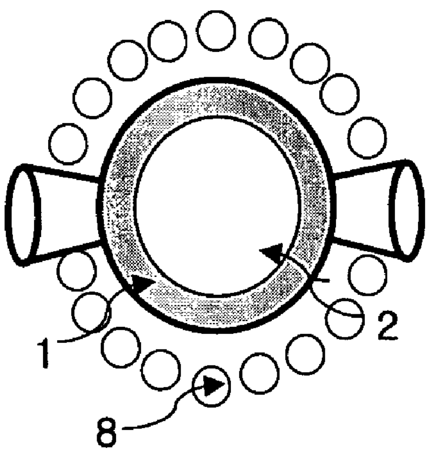

In this test, a double-layered upright-cylindrical air-lift photobioreactor, as shown in FIGS. 12*a* and 12*b*, was used, to which the gas was injected through its lower part. The light was supplied to the photobioreactor, which was emitted from an illuminant 8 installed at the exterior of the upright cylinder. A second culture region 1 to produce a useful metabolite was formed at the outer jacket region to be directly exposed to the light. A first culture region 2 to execute the vegetative cell growth was positioned at the inner core region of the second culture region. The air-lift photobioreactor was composed of an outer jacket of a capacity of 700 ml and an inner core having a capacity of 700 ml.

An aerator was installed at the lower part of each culture region. Gas supply apparatuses 5 and 6 upwardly supplied the gas to the second and first culture regions, respectively, leading to an upward flow of the culture medium. Linear fluorescent lamps 8 were used as illuminants for the supply of the light. Also, the photobioreactor was equipped with a stabilizer and an on-off switch.

*Haematococcus pluvialis* UTEX16 was used as a photosynthetic microorganism, which produces a high-value metabolite, astaxanthin. The *H. pluvialis* strain was grown in MBBM (Modified Bold's Basal Medium).

Step 1 of Batch Culture: Injection of the Photosynthetic Microorganism

The *H. pluvialis* strain UTEX16 was injected at a density of $1.2\times10^4$ cells/ml to the outer jacket (the second culture region to produce a useful metabolite) and the inner core (the first culture region to execute the vegetative cell growth) of the photobioreactor.

Step 2 of Batch Culture: Culturing of the Photosynthetic Microorganism

The light emitted from the linear fluorescent lamps 8 was irradiated to the photobioreactor at an intensity of 80 μmol/m$^2$/s for 10 days. Thereafter, the light intensity was increased to 770 μmol/m$^2$/s and maintained at the level until the next step.

In order to upwardly flow the culture fluid, mix the culture medium and supply a carbon source, gas containing 5% $CO_2$ was injected to the outer jacket and inner core at an aeration rate of 100 ml/min.

Step 1 of Continuous Culture: Transfer and Reinoculation of the Photosynthetic Microorganism After 24 days from the start of culturing, using a peristaltic pump, the photosynthetic microorganism was collected from the first and second culture regions and transferred to the second culture region to produce a useful metabolite. Then, newly subcultured cells of the microorganism were injected to the first culture region to execute the vegetative cell growth.

Step 2 of Continuous Culture: Culturing of the Photosynthetic Microorganism

The light was irradiated to the photobioreactor at a surface intensity of 770 μmol/m$^2$/s to induce the accumulation of astaxanthin by the *H. pluvialis* strain UTEX16 in the outer jacket, while simultaneously inducing the continuous growth of the *H. pluvialis* strain in the inner core (the first culture region). Herein, the initial light was attenuated to intensities suitable for the vegetative cell growth during a transmission through the outer jacket (the second culture region). Other culture conditions were identical to those as described in the second paragraph of step 2 of the batch culture.

EXPERIMENTAL EXAMPLE 1

When a photosynthetic microorganism was cultured according to steps 1 and 2 of the batch culture of the present invention, fresh cell weights and astaxanthin levels were measured.

In this test, the double-layered upright-cylindrical air-lift photobioreactor of Example 1 was used, wherein gas was injected through the lower part of the photobioreactor (see, FIGS. 12*a* and 12*b*).

*Haematococcus pluvialis* UTEX16 was used as a photosynthetic microorganism, which produces a high-value metabolite, astaxanthin ((3S,3'S)-3,3'-dihydroxy-, -carotene-4,4'-dione). The *H. pluvialis* strain was grown in MBBM (Modified Bold's Basal Medium).

The surface intensity of the outer jacket region of the photobioreactor was maintained at 80 μmol/m$^2$/s. The *H. pluvialis* strain UTEX16 was injected to the outer jacket and inner core regions at a density of $1.2\times10^4$ cells/ml.

In order to upwardly flow the culture fluid, mix the culture medium and supply a carbon source, gas containing 5% $CO_2$ was injected to the outer jacket and inner core at an aeration rate of 100 ml/min.

Under the conditions as described above, the *H. pluvialis* strain was cultured for 24 days. After two days, fresh cell weights and astaxanthin levels were measured at intervals of two days. The results are given in FIGS. 12*c* and 12*d*, in which the arrow indicates the turning point of low-intensity light to high-intensity light.

Figure 12C:
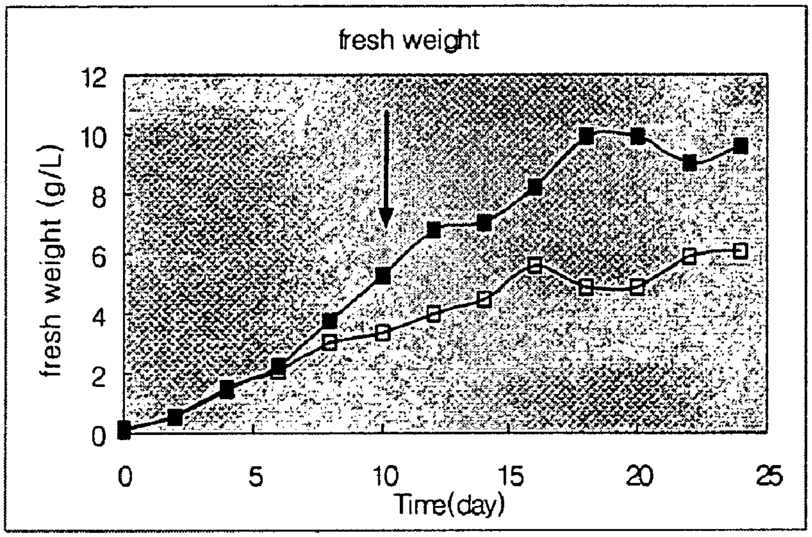
FIG. 12*c* is a graph showing a change in the fresh cell weights according to the cultivation time of Example 1 using the photobioreactor of FIG. 12*a;*
Figure 12D:
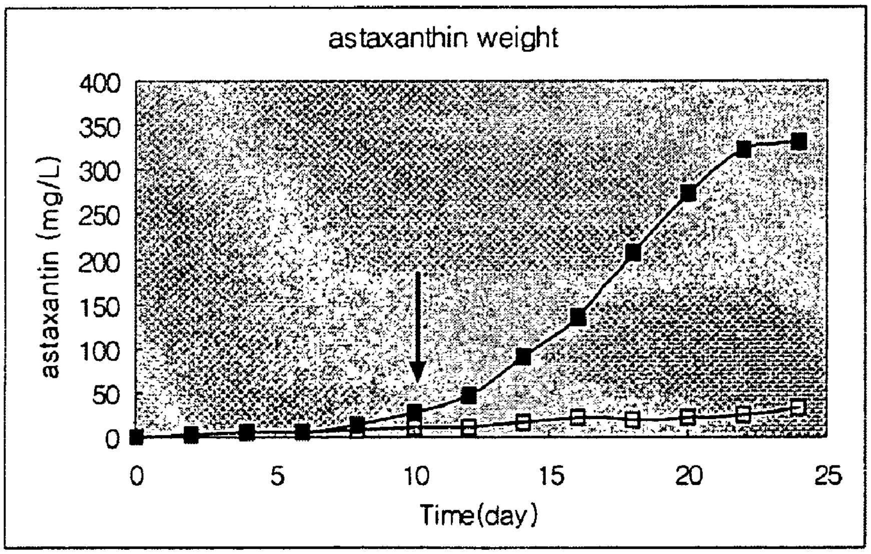
FIG. 12*d* is a graph showing a change in the astaxanthin levels according to the cultivation time of Example 1 using the photobioreactor of FIG. 12*a;*

As shown in FIGS. 12*c* and 12*d*, the *H. pluvialis* strain UTEX16 started to grow at a density similar between the outer jacket and the inner core. However, from the sixth day, the *H. pluvialis* strain UTEX16 was found to grow faster in the outer jacket than in the inner core. This is due to an increase in the shading effects by high-density biomass in the outer jacket, which leads to the insufficient light intensity for the vegetative cell growth in the inner core.

From the tenth day, the light intensity was increased to a surface intensity of 770 μmol/m$^2$/s to induce the accumulation of astaxanthin by the *H. pluvialis* strain UTEX16 in the outer jacket, while simultaneously inducing the continuous growth of the *H. pluvialis* strain in the inner core. Herein, the initial light was attenuated to intensities suitable for the vegetative cell growth during a transmission through the outer jacket. High-concentration nutrients were periodically added to the inner core for the optimal growth of the *H. pluvialis* strain, while the outer jacket was maintained under nutrient starvation condition. As shown in FIGS. 12*c* and 12*d*, in the outer jacket and the inner core, the *H. pluvialis* strain UTEX16 exhibited distinct growth rates and astaxanthin productivity. After the cultivation was completed, the *H. pluvialis* strain UTEX16 was, in the outer jacket region, found to effectively produce astaxanthin at a high concentration of 332 mg/L, be enlarged to an average size of 36.27 μm, have a final cell density of $5.8\times10^5$ cells/ml and a fresh weight of 9.94 g/L. In the inner core region, the *H. pluvialis* strain UTEX16 was steadily grown to a final cell density of $3.2\times10^5$ cells/ml with a final fresh weight of 6.1 g/L, whereas the astaxanthin production was maintained at 31 mg/L, indicating that photosynthetic microorganisms can continuously grow under conditions to inhibit the production of useful metabolites.

EXPERIMENTAL EXAMPLE 2

When a photosynthetic microorganism was cultured using a different type of the photobioreactor of the present invention, cell concentrations and astaxanthin levels were measured.

Figure 13A:
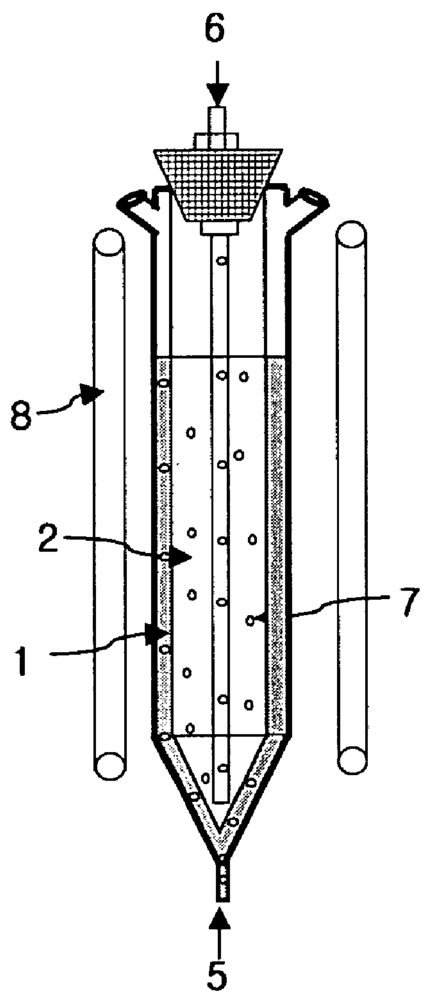
FIGS. 13*a* and 13*b* are a perspective view and a cross-sectional view of a double-layered upright-cylindrical air-lift photobioreactor with external illuminants, wherein the gas is injected to the photobioreactor through its lower part and upper part.
Figure 13B:
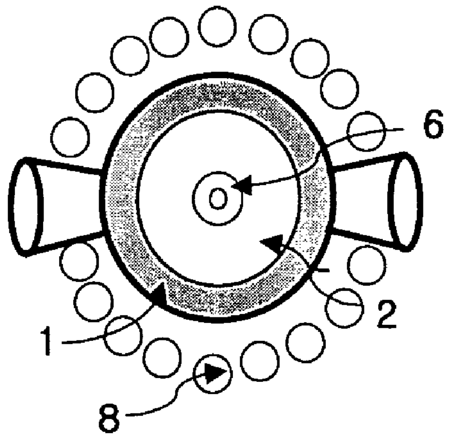
Figure 13C:
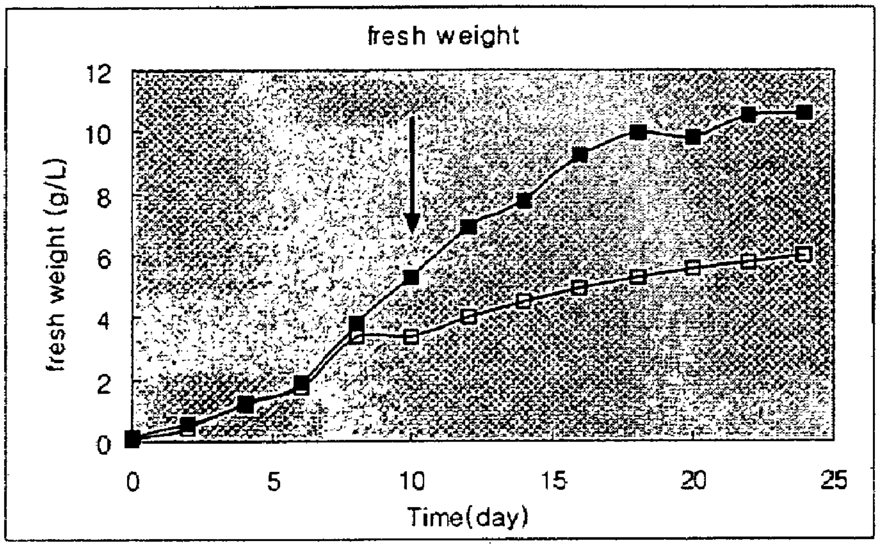
FIG. 13*c* is a graph showing a change in the fresh cell weights according to the cultivation time of Example 2 using the photobioreactor of FIG. 13*a;*
Figure 13D:
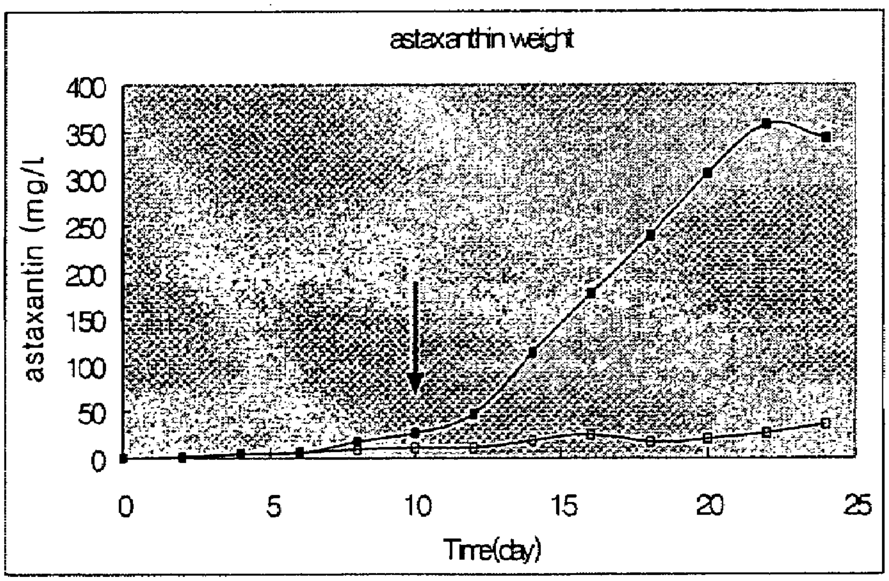
FIG. 13*d* is a graph showing a change in the astaxanthin levels according to the cultivation time of Example 2 using the photobioreactor of FIG. 13*a;*

In this test, a double-layered upright-cylindrical airlift photobioreactor, as shown in FIGS. 13*a* and 13*d*, was used. Gas was injected to the photobioreactor through its lower and upper parts. The photobioreactor, as an embodiment of the photobioreactor of the present invention, is a double-layered upright-cylinder type with an external irradiation. In the same manner as in the photobioreactor of FIGS. 12*a* and 12*b*, the photobioreactor used in this test had an internal region composed of an upright-cylindrical outer jacket corresponding to the second culture region 1 to produce a useful metabolite and an inner core corresponding to the first culture region 2 to execute the vegetative cell growth. The light enemy was supplied by linear fluorescent lamps 8 installed in the exterior of the upright cylinder. Gas supply apparatus 5 was installed at a lower part of the cylinder in order to inject gas 7 into the second culture region 1 and circulate the biomass in the culture medium by a difference in the density of the gas supply. Unlike the photobioreactor of FIGS. 12*a* and 12*b* with the gas injection unit 6 installed at its lower part, the photobioreactor used in this test was constructed to generate gas at a lower part of the inner core through an upright stainless tube installed at an upper pail of the cylinder.

The air-lift photobioreactor was composed of an outer jacket with a capacity of 500 ml and an inner core with a capacity of 500 ml.

The second culture region 1, the outer jacket, was injected with a mixed gas (5% $CO_2$) through the lower part of the air-lift photobioreactor. Also, the first culture region 2, the inner core, was injected with the mixed gas through an upright stainless steel tube, which was installed at the upper part of the cylinder and connected to the lower part of the inner core.

The same *H. pluvialis* strain and MBBM as in Example 1 were used.

A fed-batch culture was performed with an aeration rate of 100 ml/min in each of the outer jacket and inner core.

Linear fluorescent lamps were used as external illuminants for the supply of the light. The initial light was irradiated to the outer jacket with a surface intensity of 80 $\mu mol/m^2/s$. From the tenth day, the light intensity was increased to 770 $\mu Mol/m^2/s$ to induce the accumulation of astaxanthin in the outer jacket, while simultaneously inducing the continuous vegetative growth of the *H. pluvialis* strain in the inner core.

Under the conditions as described above, the *H. pluvialis* strain was cultured for 24 days. After two days, fresh cell weights and astaxanthin levels were measured at intervals of two days. The results are given in FIGS. 13*c* and 13*d*, in which the arrow indicates the turning point of low-intensity light to high-intensity light.

As shown in FIGS. 13*c* and 13*d*, after the cultivation was completed, in the outer jacket region, the *H. pluvialis* strain UTEX16 was found to effectively produce astaxanthin at a high concentration of 356 mg/L. The final astaxanthin level in the outer jacket region was about 10-fold higher than that in the inner core region. These results indicate that the double-layered photobioreactor, which includes the outer jacket region to produce the astaxanthin production and the inner core region to execute the vegetative cell growth, is applicable for the cultivation of photosynthetic microorganisms.

EXPERIMENTAL EXAMPLE 3

A continuous culture was carried out using the photobioreactor of the present invention, in which a photosynthetic microorganism of different densities was inoculated to an outer jacket and an inner core of the photobioreactor.

In this test, a double-layered upright-cylindrical air-lift photobioreactor, as shown in FIGS. 13*a* and 13*d*, was used. Gas was injected to the photobioreactor through its lower and upper parts. An illuminant was installed at the exterior of the photobioreactor. The air-lift photobioreactor was composed of an outer jacket with a capacity of 500 ml and an inner core with a capacity of 500 ml.

The second culture region 1, the outer jacket, was injected with a mixed gas (5% $CO_2$) through the lower part of the air-lift photobioreactor. Also, the first culture region 2, the inner core, was injected with the mixed gas through an upright stainless steel tube which was installed at the upper part of the cylinder and connected to the lower part of the inner core.

The same *H. pluvialis* strain and MBBM as in Example 1 were used. The outer jacket was inoculated with biomass of $2.5\times10^5$ cells/ml which was collected from the inner core of Experimental Examples 1 and 2, while the inner core was inoculated with newly subcultured *H. pluvialis* UTEX16 of $1.0\times10^5$ cells/ml.

A fed-batch culture was performed with an aeration rate of 100 ml/min in each of the outer jacket and inner core.

Linear fluorescent lamps were used as external illuminants for the supply of the light. The initial light was irradiated to the outer jacket with a surface intensity of 200 $\mu mol/m^2/s$. Since the initial light was transmitted through the outer jacket containing the biomass, the light intensity at a surface of the inner core was maintained at 40 $\mu mol/m^2/s$.

Under the conditions as described above, the *H. pluvialis* strain was cultured for 16 days. After one day, fresh cell weights and astaxanthin levels were measured everyday. The results are given in FIGS. 14*a* and 14*b*.

Figure 14A:
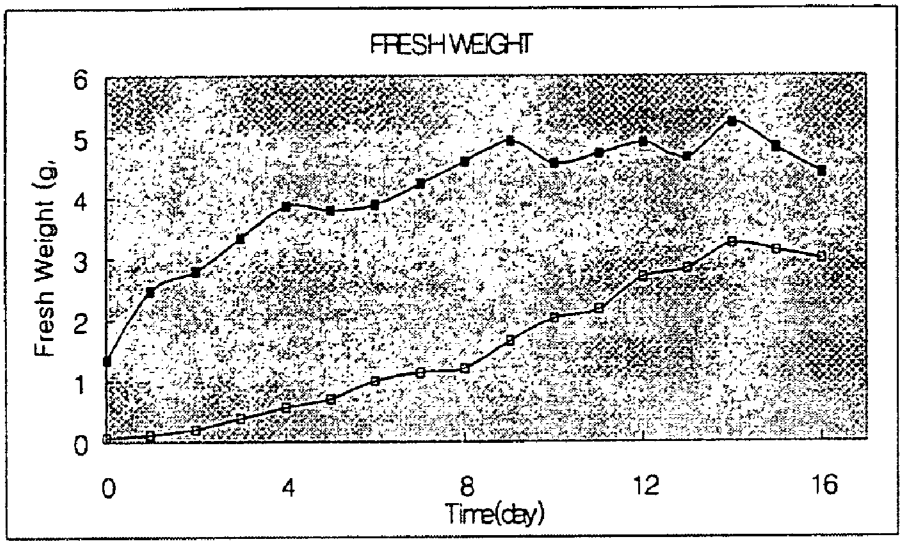
FIG. 14*a* is a graph showing a change in the fresh cell weights according to the cultivation time of Example 3 using the photobioreactor of FIG. 13*a*.
Figure 14B:
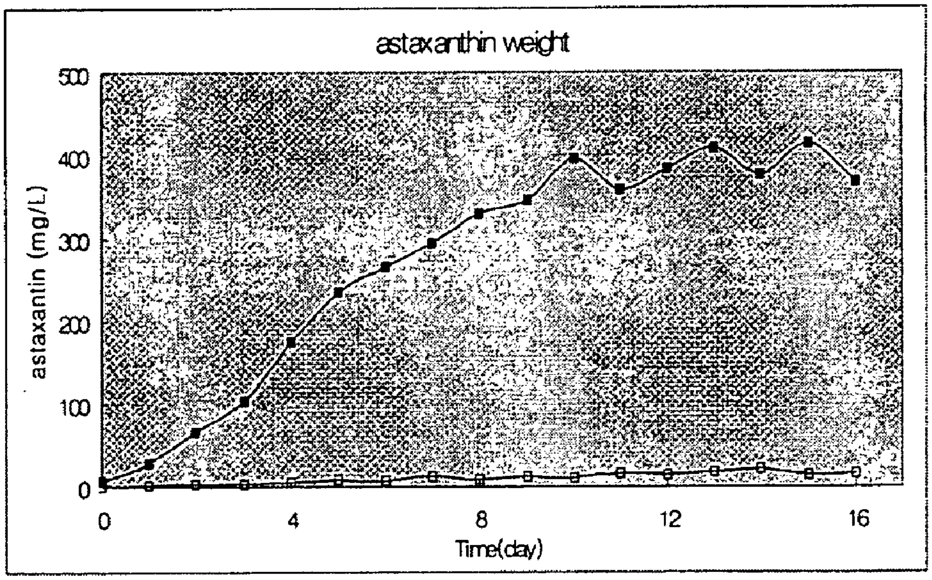
FIG. 14*b* is a graph showing a change in the astaxanthin levels according to the cultivation time of Example 3 using the photobioreactor of FIG. 13*a*.

FIG. 14*a* shows the change in fresh cell weights according to the time in the first and second culture regions 2 and 1 of the photobioreactor, while FIG. 14*b* displays the change in astaxanthin levels according to the time in each culture region. After the cultivation was completed, in the outer jacket region, the *H. pluvialis* strain UTEX16 was found to effectively produce astaxanthin at a high concentration of 356 mg/L. The final astaxanthin level in the outer jacket region was about 24.5-fold higher than that in the inner core region. In the inner core region, the *H. pluvialis* strain UTEX16 was steadily grown to a final cell density of $3.5\times10^5$ cells/ml with a final fresh weight of 3.01 g/L, whereas the astaxanthin production was maintained at 15 mg/L, indicating that photosynthetic microorganisms can continuously grow under conditions to inhibit the production of useful metabolites.

From the above cultivation process, the biomass in the outer jacket will be subjected to a downstream process for isolating the produced useful metabolite, while the biomass in the inner core to execute the vegetative cell growth will be utilized as an inoculum for the outer jacket in the next culture run. Thus, the inner core is inoculated with newly subcultured cells of a photosynthetic microorganism, while the outer jacket is inoculated with the biomass grown in the inner core of the previous culture. Therefore, the present photobioreactor and method make it possible to perform the conventional two-stage culture process in a single bioreactor.

INDUSTRIAL APPLICABILITY

As described hereinbefore, the present multi-layered photobioreactor and method of culturing a photosynthetic microorganism using the same allow the conventional two-stage culture process to be performed in a single bioreactor. That is, the characteristic structure of the multi-layered photobioreactor with the two culture regions to execute the vegetative cell growth and produce a useful metabolite, respectively, which are formed in the inner part of the photobioreactor, simplifies the two-stage bioprocess by separately performing the rapid culturing of a photosynthetic microorganism to high density and the production of a useful metabolite. Thus, using the light emitted from a single light source, the vegetative cell growth can be achieved simultaneously with the production of a useful metabolite in the photobioreactor. In addition, the photobioreactor has economical benefits in that it does not require many personnel for the vegetative cell growth and induction of useful metabolites and reduces land cost, installation cost, operation cost and electrical cost.

The invention claimed is:

1. A method of culturing a photosynthetic microorganism with a multi-layered photobioreactor, comprising:

(a) injecting a photosynthetic microorganism to a first culture region to execute vegetative cell growth and a second culture region to produce a useful metabolite, wherein the first and second culture regions are equipped in the multi-layered photobioreactor (step 1);

(b) irradiating light to the second culture region to proliferate the photosynthetic microorganism (step 2); and (c) harvesting the cultured photosynthetic microorganism from the first and second culture regions (step 3), wherein the multi-layered photobioreactor comprises:

at least one first culture region containing both a microorganism and a culture medium therein to execute vegetative growth of the microorganism;

at least one second culture region closely layered on a side surface of the first culture region and containing both a culture medium and a microorganism therein to produce a useful metabolite; and a transparent partition placed between the first and second culture regions to separate the first and second culture regions from each other, and the first and second culture regions are provided in an inside portion and an outside portion of the photobioreactor, respectively, to allow sun light or artificial light irradiated to the photobioreactor for cultivation to sequentially pass through the second culture region and the transparent partition to reach the first culture region; and a plurality of the photobioreactors as unit modules are spatially arranged to produce another photobioreactor.

2. A method of culturing a photosynthetic microorganism with a multi-layered photobioreactor, comprising:

(a) transferring a photosynthetic microorganism grown in a first culture region to execute vegetative cell growth by a batch culture to a second culture region to produce a useful metabolite, wherein the first and second culture regions are equipped in the photobioreactor, and injecting newly subcultured cells of the photosynthetic microorganism into the first culture region (step 1);

(b) irradiating light to the second culture region to proliferate the photosynthetic microorganism and accumulate the useful metabolite (step 2); and (c) harvesting the photosynthetic microorganism from the second culture region and repeating the steps 1 and 2 by transferring all or a portion of the photosynthetic microorganism grown in the first culture region to the second culture region (step 3), wherein the in multi-layered photobioreactor comprises:

at least one first culture region containing both a microorganism and a culture medium therein to execute vegetative growth of the microorganism;

at least one second culture region closely layered on a side surface of the first culture region and containing both a culture medium and a microorganism therein to produce a useful metabolite; and a transparent partition placed between the first and second culture regions to separate the first and second culture regions from each other, and the first and second culture regions are provided in an inside portion and an outside portion of the photobioreactor, respectively, to allow sun light or artificial light irradiated to the photobioreactor for cultivation to sequentially pass through the second culture region and the transparent partition to reach the first culture region; and a plurality of the photobioreactors as unit modules are spatially arranged to produce another photobioreactor.

3. A method according to claim 1, wherein the method comprises selectively supplying to the first or second culture region of the photobioreactor a nutrient that has been exhausted with time upon cultivation using the photobioreactor.

4. The method according to claim 1, wherein, at the step 2, the light is initially supplied at an intensity capable of forming an optimal condition for the vegetative growth of the photosynthetic microorganism until the photosynthetic microorganism reaches a stationary phase, and then is supplied at an intensity capable of forming a stressed condition for production of the useful metabolite.

5. The method according to claim 2, wherein, at the step 3, the photosynthetic microorganism is transported by a peristaltic pump or air pressure.

6. The method according to claim 2, wherein, at the step 2, the light is controlled to an intensity capable of forming a stressed condition for the production of the useful metabolite.

7. The method according to claim 1, wherein the photosynthetic microorganism is selected from the group consisting of *Haematococcus* sp., *Dunaliella* sp., *Chlorococcum* sp., *Chlorella* sp., *Acetabularia* sp., *Microcystis* sp., *Nostoc* sp., and *Oscillatoria* sp.

8. The method according to claim 4, wherein the intensity capable of forming an optimal condition for the vegetative growth of the photosynthetic microorganism is 40-200 μmol/$m^2$/s, and the intensity capable of forming a stressed condition is 200-2000 μmol/$m^2$/s.

9. The method according to claim 1, wherein the multi-layered photobioreactor further comprises a light irradiation unit to supply light energy to the in microorganism in the photobioreactor.

10. The method according to claim 9, wherein the second culture region of the multilayered photoreactor to produce a useful metabolite is formed at an outmost surface of the photobioreactor, and sunlight is thus irradiated to the second culture region at the outmost surface of the photobioreactor.

11. The method according to claim 9, wherein the light irradiation unit is one or more selected from the group consisting of fluorescent lamps, halogen lamps, optical fibers, neon tubes and light-emitting diodes.

12. The method according to claim 9, wherein the light irradiation unit of the photobioreactor comprises a plurality of independent units which are independently operated.

13. The method according to claim 1, wherein the shape of the photobioreactor is selected from the group consisting of a rectangular flat-plate shape, a cylindrical shape, a tubular shape and other three-dimensional shapes.

14. The method according to claim 1, wherein the photobioreactor further comprises gas injection unit to inject gas into the first and second culture regions.

15. The method according to claim 1, wherein the photobioreactor is arranged in a one-dimensional, two-dimensional or three-dimensional consecutive arrangement.

16. The method according to claim 1, wherein the photobioreactor is equipped with a temperature control unit and a sun screen unit.

* * * * *